(12) United States Patent
Splieth et al.

(10) Patent No.: US 9,011,549 B2
(45) Date of Patent: Apr. 21, 2015

(54) EXPANDING TRIAL STEM FOR ORTHOPAEDIC SURGERY

(75) Inventors: Roy Philip Splieth, Central Valley, NY (US); Shawn Michael Kroll, Waldwick, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 103 days.

(21) Appl. No.: 13/525,788

(22) Filed: Jun. 18, 2012

(65) Prior Publication Data

US 2012/0259334 A1 Oct. 11, 2012

Related U.S. Application Data

(62) Division of application No. 11/503,459, filed on Aug. 11, 2006, now Pat. No. 8,216,320.

(51) Int. Cl.
| | | |
|---|---|---|
| *A61F 2/32* | (2006.01) | |
| *A61F 2/46* | (2006.01) | |
| *A61F 2/36* | (2006.01) | |
| *A61F 2/30* | (2006.01) | |

(52) U.S. Cl.
CPC ............. *A61F 2/4684* (2013.01); *A61F 2/36* (2013.01); *A61F 2002/30579* (2013.01); *A61F 2002/30594* (2013.01); *A61F 2002/3082* (2013.01); *A61F 2002/30822* (2013.01)

(58) Field of Classification Search
CPC .................................. A61F 2/32; A61F 2/3662
USPC ............... 623/63, 65, 68, 310, 313, 314, 320, 623/22.12, 22.41, 22.43, 22.46, 22.11, 22.4, 623/23.15, 23.19, 23.26, 23.27; 606/22.12, 606/22.41, 22.43, 22.46, 63, 65, 68, 310, 606/313, 314, 320
See application file for complete search history.

(56) References Cited

U.S. PATENT DOCUMENTS

| | | | |
|---|---|---|---|
| 2,381,050 A | 8/1945 | Hardnige | |
| 2,473,968 A | 6/1949 | Paton | |
| 2,490,364 A | 12/1949 | Livingston | |
| 3,759,257 A | * 9/1973 | Fischer et al. | 606/63 |
| 3,801,989 A | 4/1974 | McKee | |
| 3,846,846 A | 11/1974 | Fischer | |
| 3,846,848 A | 11/1974 | McNair | |
| 4,091,806 A | 5/1978 | Aginsky | |
| 4,520,511 A | * 6/1985 | Gianezio et al. | 623/22.46 |

(Continued)

OTHER PUBLICATIONS

Zimmer® Trabecular Metal™ Humeral Stem Four-Part Fracture Surgical Technique. pp. 1-17, 2005.

*Primary Examiner* — Thomas J Sweet
*Assistant Examiner* — Christopher D Prone
(74) *Attorney, Agent, or Firm* — Lerner, David, Littenberg, Krumholz & Mentlik, LLP

(57) ABSTRACT

A trial device and a method for using the device in surgery are disclosed. The device includes a body including a proximal portion and a distal portion. The proximal portion has a post or trunion projecting therefrom. The distal portion extends from the proximal portion and includes a first arm and a second arm, the first and second arms being movable with respect to one another. The body further includes a cavity formed therein so as to extend through the proximal portion and into the distal portion. The device further includes a driver adapted for sliding engagement within the internal cavity of the body such that movement of the driver, preferably in a distal direction, causes movement of a portion of the first arm away from a portion of the second arm.

21 Claims, 8 Drawing Sheets

(56) References Cited

U.S. PATENT DOCUMENTS

| | | | |
|---|---|---|---|
| 5,002,581 A * | 3/1991 | Paxson et al. | 623/22.44 |
| 5,032,133 A | 7/1991 | Carbone | |
| 5,314,489 A | 5/1994 | Hoffman et al. | |
| 5,441,500 A | 8/1995 | Seidel et al. | |
| 5,644,439 A | 7/1997 | Shiba et al. | |
| 5,888,208 A * | 3/1999 | Ro | 623/23.15 |
| 6,355,069 B1 * | 3/2002 | DeCarlo et al. | 623/23.26 |
| 6,613,093 B2 | 9/2003 | DeCarlo, Jr. et al. | |
| 7,044,975 B2 | 5/2006 | Cheal et al. | |
| 2004/0030401 A1 | 2/2004 | Hassler et al. | |
| 2005/0049713 A1 * | 3/2005 | Garber et al. | 623/22.21 |

* cited by examiner

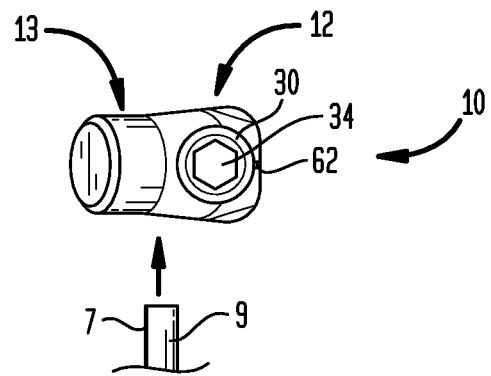
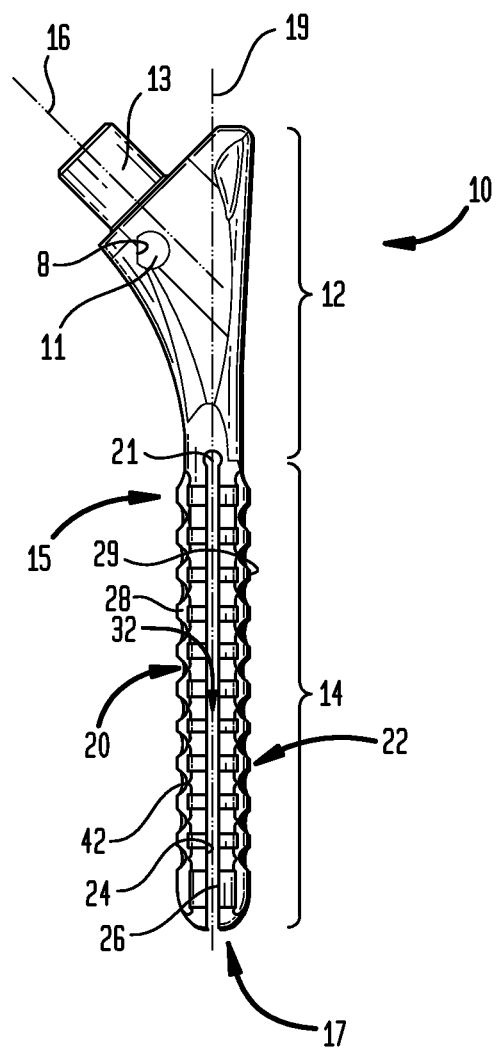

FIG. 5
FIG. 6
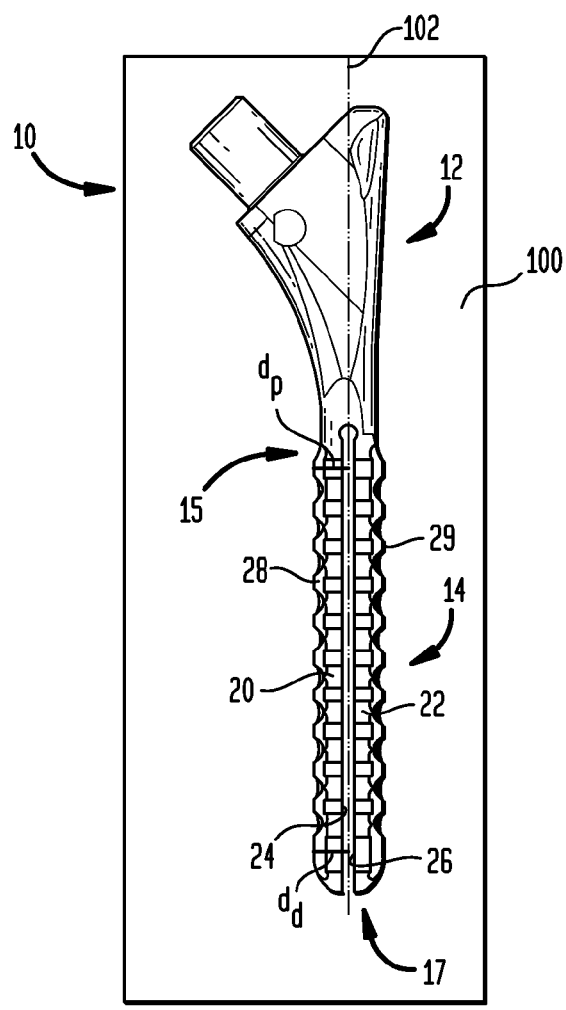
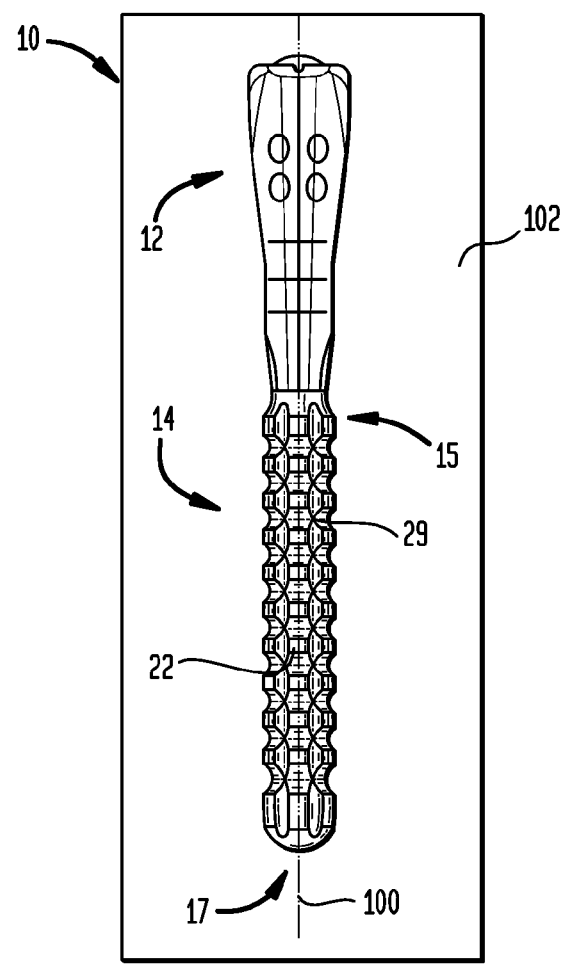
FIG. 7
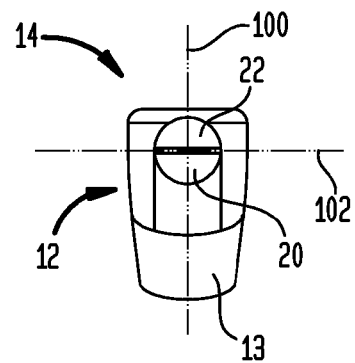

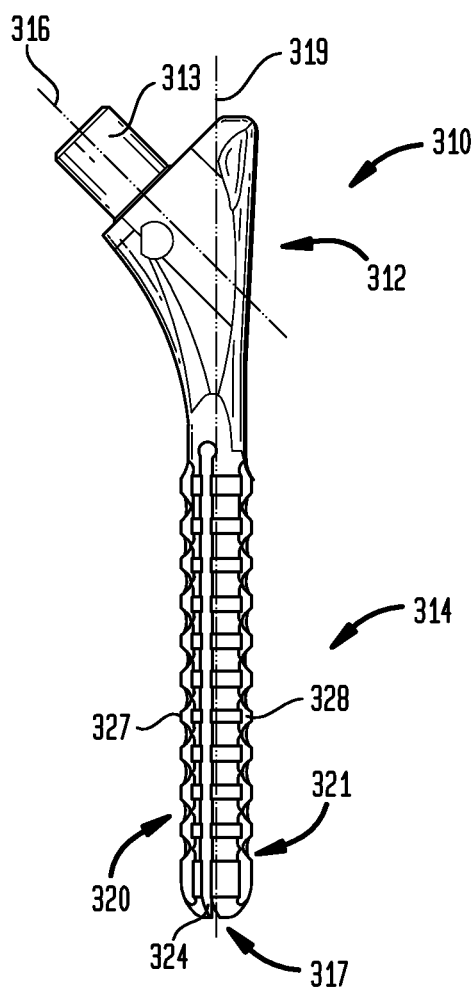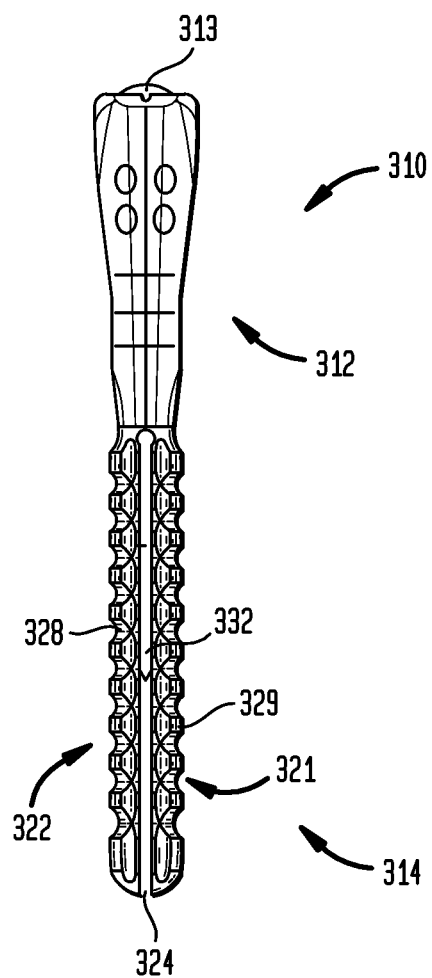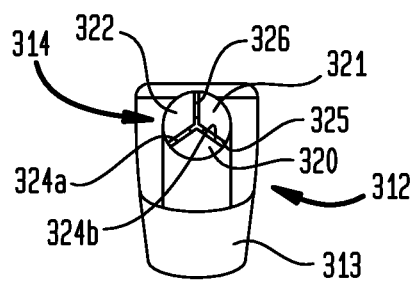

EXPANDING TRIAL STEM FOR ORTHOPAEDIC SURGERY

CROSS-REFERENCE TO RELATED APPLICATIONS

The present application is a divisional of U.S. patent application Ser. No. 11/503,459, filed Aug. 11, 2006, now U.S. Pat. No. 8,216,320, the disclosure of which is incorporated herein by reference.

BACKGROUND OF THE INVENTION

A joint replacement procedure is sometimes necessary to repair a joint having a diseased or damaged articulating surface. Such a procedure involves removal of the diseased or damaged portions of the joint and replacing them with a prosthetic implant. This is often a desirable procedure for ball-and-socket type joints, particularly the shoulder and hip joints. A shoulder joint replacement procedure, for example, often involves removal of the humeral head and replacement thereof with an implant including a stem and a head. It is important that the implant be positioned correctly within the joint in order to ensure that appropriate joint kinematics, including range of motion, are preserved so as to replicate, as closely as possible, those of the original joint.

The structure of prosthetic joint components has been developed to be suited for permanent implantation into the joint and includes features that may promote bony ingrowth, adhesion using cement, press-fit or a combination thereof. Particularly, in the case of implants including a stem, such as those used in shoulder arthroplasty, these features are included on the outside surface of the stem. Such features are not well-suited for use during the assessment of joint kinematics. Accordingly, instruments to be used in this part of the procedure have been developed. For shoulder arthroplasty, two general types of such devices have been developed, both of which are affixed to the bone during joint kinematic evaluation and removed therefrom after a proper position for the implant has been determined.

One such device is an externally-fixated jig. These devices, however tend to be bulky, complex and time consuming to set up and use. They also require the use of external fixation devices and/or power tools that introduce further complications to the surgical procedure. Because these devices exit through the incision to the outside of the body they are generally cumbersome, making accurate range of motion assessment difficult. Such jigs are shown in U.S. Pat. Nos. 6,267,785 and 6,193,758.

An additional or alternative device is a trial. Typically, these devices are designed to correspond to an implant in size and shape. The trial is designed to be temporarily inserted into a prepared medullary canal of the humerus in a manner similar to that of an implant. Known trials are typically used in conjunction with a lap sponge that is temporarily wrapped around the distal portion of the trial. The sponge-wrapped trial is then wedged into the canal, the sponge promoting a pressure fit therebetween, to evaluate the appropriate position for the implant. In the alternative, a foam ring can be assembled onto the trial stem as discussed in the brochure entitled Zimmer Trabecular Metal™ Humeral Stem Four-Part Fracture Surgical Technique, available from Zimmer, Inc., P.O. Box 708, 1800 West Center Street, Warsaw, Ind. 46581-0708. While eliminating the problems associated with externally-fixated devices, known trials present other problems. For example, by positioning a resilient material, such as a sponge, between the inside surface of the prepared medullary canal and the trial stem, the stem may be allowed to move within the joint leading to an unreliable joint kinematics assessment. Additionally, the use of a lap sponge to hold the trial within the medullary canal leads to a risk of leaving sponge or cloth debris behind in the bone after the trial is removed.

It is therefore necessary to provide a device that can be used for improved assessment of joint kinematics during a joint arthroplasty procedure conducted on a joint.

SUMMARY OF THE INVENTION

The present invention relates to a trial device for use in surgery. The device includes a body including a proximal portion and a distal portion. The proximal portion has a post or trunion projecting therefrom. The distal portion extends from the proximal portion and includes a first arm and a second arm, the first and second arms being movable with respect to one another. The body further includes a cavity formed therein so as to extend through the proximal portion and into the distal portion. The device further includes a driver adapted for sliding engagement within the internal cavity of the body such that movement of the driver, preferably in a distal direction, causes movement of a portion of the first arm away from a portion of the second arm.

In one embodiment the distal portion of the body includes an outer bone-engaging surface, which may be formed from a plurality of intersecting grooves. In a preferred embodiment, a portion of the bone engaging surface extends along a portion of the first arm in an arcuate fashion between a first edge of the first face and a second edge of the first face, and a portion of the bone engaging surface extends along a portion of the second arm in an arcuate fashion between a first edge of the second face and a second edge of the second face. The portion of the bone engaging surface which extends along the first arm preferably forms a first apex opposite the first face extending substantially in a proximal-distal direction, and the portion of the bone engaging surface which extends along the second arm preferably forms a second apex opposite the second face extending substantially in a proximal-distal direction. Further preferably, the movement of the driver in a distal direction causes movement of the first arm and second arm from a first position, in which the first apex and the second apex form an angle therebetween having an intersection spaced distally from the body, to a second position, in which the first apex and the second apex are substantially parallel.

A further embodiment of the present invention relates to a method for performing a joint replacement surgery. The method includes introducing the trial device into a joint such that at least a portion of the trial extends into to a prepared bone canal associated with the joint. The trial is adapted to fit within the bone canal and has an expandable bone engaging surface and a feature which is operable to cause expansion of the bone engaging surface. The method further includes manipulating the implant into a first position within the joint and temporarily securing the implant within the joint by operating the feature of the implant so as to cause the bone engaging surface to expand and engage an interior surface of the prepared bone canal.

The trial provided in the method of the present embodiment may also be such that the feature of the trial is further operable to reverse the expansion caused of the trial. The method may include operating the feature of the trial to reverse the expansion of the bone engaging surface. The method may further include manipulating the trial into a second position within the joint, and temporarily securing the trial within the joint by operating the feature of the trial so as to cause the bone engaging surface to re-engage the interior surface of the prepared bone canal. The trial associated with the method of the present embodiment may further include a visual indicia relating to the position of the trial within the joint. The method may, accordingly, include the step of using the indicia to establish a location of the trial relative to the joint.

The method further includes removing the trial implant from the joint and providing an implant corresponding in size to a size of the trial and includes indicia that correspond to the indicia of the trial. The implant is then introduced into the joint such that at least a portion of the implant extends into the prepared bone canal.

A further embodiment relates to a method for performing surgery. The method includes introducing a trial into a joint such that at least a portion of the trial extends into a prepared bone canal associated with the joint, the trial being adapted to fit within the prepared bone canal and having a proximal portion and a distal portion. The distal portion includes an expandable bone engaging surface formed over a first arm and a second arm, the first and second arms extending from the proximal portion of the trial. The trial further includes a cavity extending through the proximal portion and into the distal portion and a driver adapted for sliding engagement within the internal cavity. The method further includes manipulating the trial into a first position within the prepared bone canal and temporarily securing the trial within the prepared bone canal by moving the driver distally within the cavity so as to cause a portion of the first arm and a portion of the second arm to move outwardly away from one another such that the expandable bone engaging surface engages an interior surface of the prepared bone canal.

BRIEF DESCRIPTION OF THE DRAWINGS

The present invention will be better understood on reading the following detailed description of nonlimiting embodiments thereof, and on examining the accompanying drawings, in which:

FIG. 1 is a top view of a trial according to an embodiment of the present disclosure;

FIGS. 2 and 3 are elevation views of a trial according to an embodiment of the present disclosure;

FIGS. 5 and 6 are elevation views of a trial according to an embodiment of the present invention, wherein a first plane lying on the medial-lateral and proximal-distal axes and a second plane lying on the anterior-posterior and proximal-distal axes intersect the trial;

FIG. 7 is a bottom view of the planes shown in FIGS. 5 and 6 intersecting a trial according to an embodiment of the present invention.

FIGS. 12 and 13 are elevation views of a trial according to an embodiment of the present invention;

FIG. 14 is a bottom view of the trial shown in FIGS. 12 and 13; and

DETAILED DESCRIPTION

Figure 3:
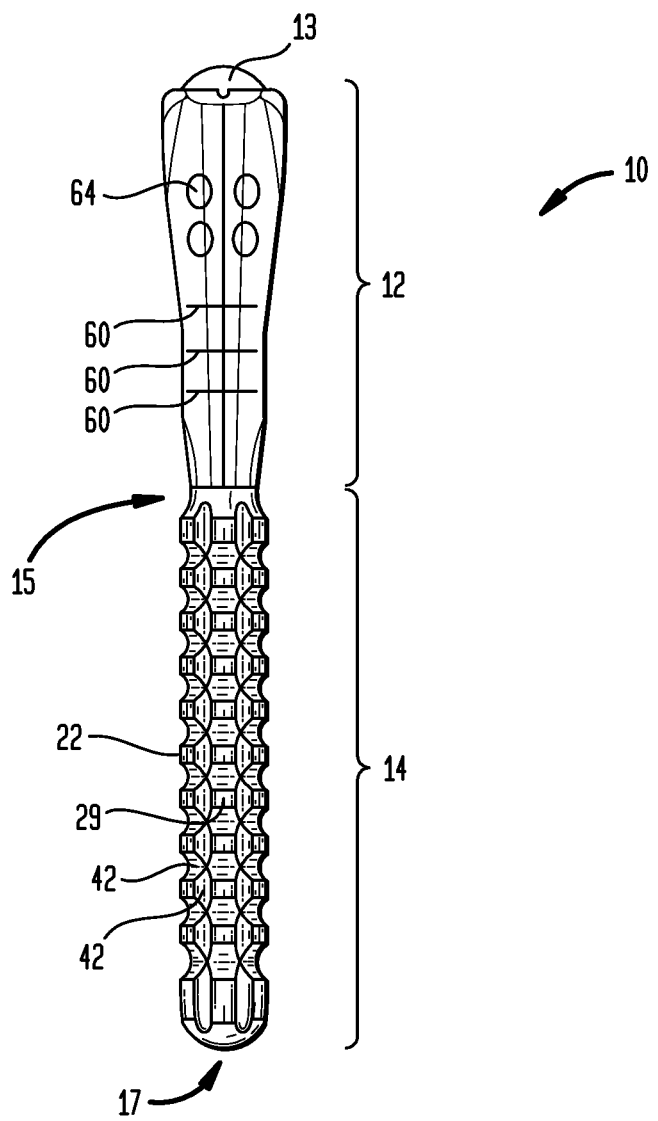

Referring to the drawings, wherein like reference numerals represent like elements, there is shown in FIGS. 1-4, in accordance with one embodiment of the present invention, a trial, designated generally by reference numeral 10. In describing preferred embodiments of trial 10, reference will be made to the directional nomenclature used in describing the human body. It is noted that this nomenclature is used only for convenience and that it is not intended to be limiting with respect to the scope or structure of the invention. When referring to specific directions, the device is understood to be described only with respect to its orientation and position during an exemplary application to the human body. As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

It is further noted that, although the present invention is shown and described with respect to a humeral trial, it is understood that particular aspects of the present invention can be applied to additional devices. Such devices generally include humeral implants and both femoral implants and femoral trials.

Returning now to FIGS. 1-4, an exemplary embodiment of trial 10 is shown as one which is adapted for insertion into the proximal portion of a prepared humerus and includes a proximal portion 12 and a distal portion 14. Proximal portion 12 includes post 13 which is structured to receive a trial humeral head (not shown) to be used during trialing of the joint using trial 10. Distal portion 14 of trial 10 projects along a longitudinal axis thereof from proximal portion 12 generally in the proximal-distal direction. Distal portion 14 is structured to fit within a prepared bone canal, preferably the medullary canal of the humerus. Post 13 has a longitudinal axis 16 that is angled with respect to the longitudinal axis 19 of distal portion 14 so as to substantially replicate the typical geometry of the prepared bone.

Figure 4:
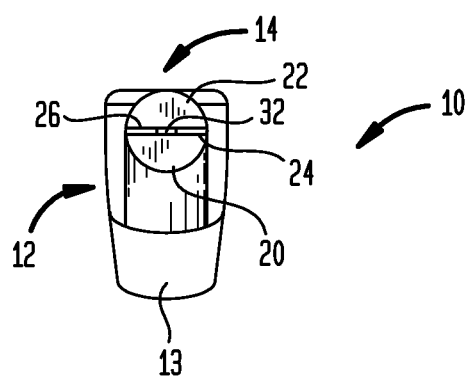
FIG. 4 is a bottom view of a trial according to an embodiment of the present invention.

Distal portion 14 includes a first arm 20 and a second arm 22 that are positioned adjacent to each other. Arms 20, 22 each have a respective inwardly-directed face 24, 26, which is generally planar and lies along the anterior-posterior and proximal-distal directions. First and second arms 20, 22 each further include a respective outside surface 28, 29 which forms a substantially semi-circular cross-section (as shown in FIG. 4) along a plane normal to the longitudinal axis of distal portion 14. First arm 20 and second arm 22 are designed to be movable with respect to one another between a first position and a second position. The movement of first and second arms 20, 22 results in expansion of the distal portion 14 whereby a point along the outside surface 28 of first arm 20 moves away from a point along the outside surface 29 of second arm 22 in a direction lying in a plane defined by the medial-lateral and anterior-posterior axes, i.e. parallel to the frontal plane. In an alternative embodiment, first and second faces 24, 26 may be positioned so as to lie along medial-lateral and proximal-distal axes. In such an embodiment, the movement of first and second arms occurs along a plane lying along an anterior-posterior axis and a proximal-distal axis.

In a preferred embodiment, when first and second arms 20, 22 are in the first position, first and second faces 24, 26 are generally parallel to each other and are spaced apart from each other at a predetermined distance. Preferably the distance between faces 24 and 26 is about 0.055" to 0.073". Further preferably, when arms 20, 22 are in the second position, faces 24, 26 are angled with respect to one another. The angle formed by first and second faces 24, 26 preferably has an apex located proximally of distal portion 14 and has a value of between 0.5o and 2o. More preferably, the value of the angle formed between first and second faces 24, 26 is about 1o.

As shown in FIGS. 5-7, outside surfaces 28 and 29 are preferably tapered along first plane 100 such that a point on outside surface 28 near the tip 17 of distal portion 14 intersecting first plane 100 is spaced apart from second plane 102 at a distance dd, and a point on outside surface 28 near proximal end 15 of distal portion 14 intersecting first plane 100 is spaced apart from second plane 102 by a distance dp. Preferably, dd is less than dp by an amount of between 1 mm and 0.25 mm. More preferably, dd is less than dp by a distance of about 0.5 mm. Preferably, outside surface 29 of second arm 22 is tapered so as to substantially match the taper of first arm 20. Preferably, distal portion 14 is tapered along plane 102 by an amount less than that of the taper along plane 100. Further, distal portion 14 may not be tapered along plane 102. The amount of the taper formed in outside surfaces 28, 29 along additional planes (not shown) located between the first and second planes and extending through the longitudinal axis of distal portion 14 vary such that those closer to the first plane 100 will have a greater taper than those closer to the second plane 102 such that distal portion 14 has an oblong cross-sectional shape near tip 17.

Furthermore, outside surfaces 28, 29 are preferably shaped such that, during expansion thereof, arms 20, 22 can be positioned relative to each other such that outside surfaces 28, 29 together form a substantially cylindrical shape. In such a position, dp is substantially equal to dd, each being substantially equal to the radius of a cylinder having a center along the longitudinal axis of distal portion 14. Furthermore, in this position, substantially all points lying along outside surfaces 28, 29 of arms 20, 22 are spaced apart from the longitudinal axis of distal portion 14 at a distance equal to that of the radius of the cylinder. In order for distal portion to form such a shape while arms 20, 22 are in the second position, it may be necessary to form outside surfaces 28, 29 such they have a taper along plane 102.

The movement of first arm 20 and second arm 22 is preferably achieved by bending of first arm 20 and second arm 22 in their respective directions of movement. In order to allow first and second arms 20, 22 to bend as such, distal portion 14 of trial 10 is preferably designed to provide adequate strength to allow for trial 10 to be secured within the bone canal during trialing, and should be somewhat flexible to allow arms 20, 22 to move when a force is applied thereto. Further preferably, first and second arms 20, 22 bend substantially only near proximal end 15 of distal portion 14 such that first and second faces 24, 26 remain substantially planar when first and second arms 20, 22 are in the second position. Such flexing of arms 20, 22 can be accomplished by forming distal portion 14 such that the structure thereof is weaker in the area where bending is desired. The area of bending can, for example, be formed such that proximal end 15 of distal portion 14 is thinner in diameter than the remainder of distal portion 14. Further, the area of bending can also include hole 21 at the point where arms 20, 22 extend from proximal portion 12. Hole 21 reduces the stress concentration at this location within trial 10 and allows for repeated flexing of arms 20, 22 with a reduced risk of formation of cracks which can propagate into proximal portion 12 and cause breakage of trial 10. Hole 21 further provides a more flexible point within the structure of trial 10 where arms 20, 22 can bend.

In order to cause movement of arms 20, 22 a cavity (shown in FIGS. 8-10), preferably in the form of hole 30 is formed within trial 10 along the longitudinal axis of distal portion 14. Hole 30 preferably extends through proximal portion 12 of trial 10 and into distal portion 14. The portion of hole that is formed in distal portion 14 of trial 10 extends partially into first arm 20 and partially into second arm 22. Hole 30 is adapted to receive driver 32, which is preferably substantially cylindrical in shape. Preferably, driver 32 includes a threaded portion 31 and mates for threading engagement with a threaded portion 33 included within proximal portion 12 of trial 10 such that turning driver 32 with respect to hole 30 causes advancement and withdrawal of driver 32 within hole 30. Driver 32 preferably further includes a head 34 (shown in FIG. 8) adapted to be used in conjunction with an instrument such as a hex wrench or a screwdriver.

Figure 8:
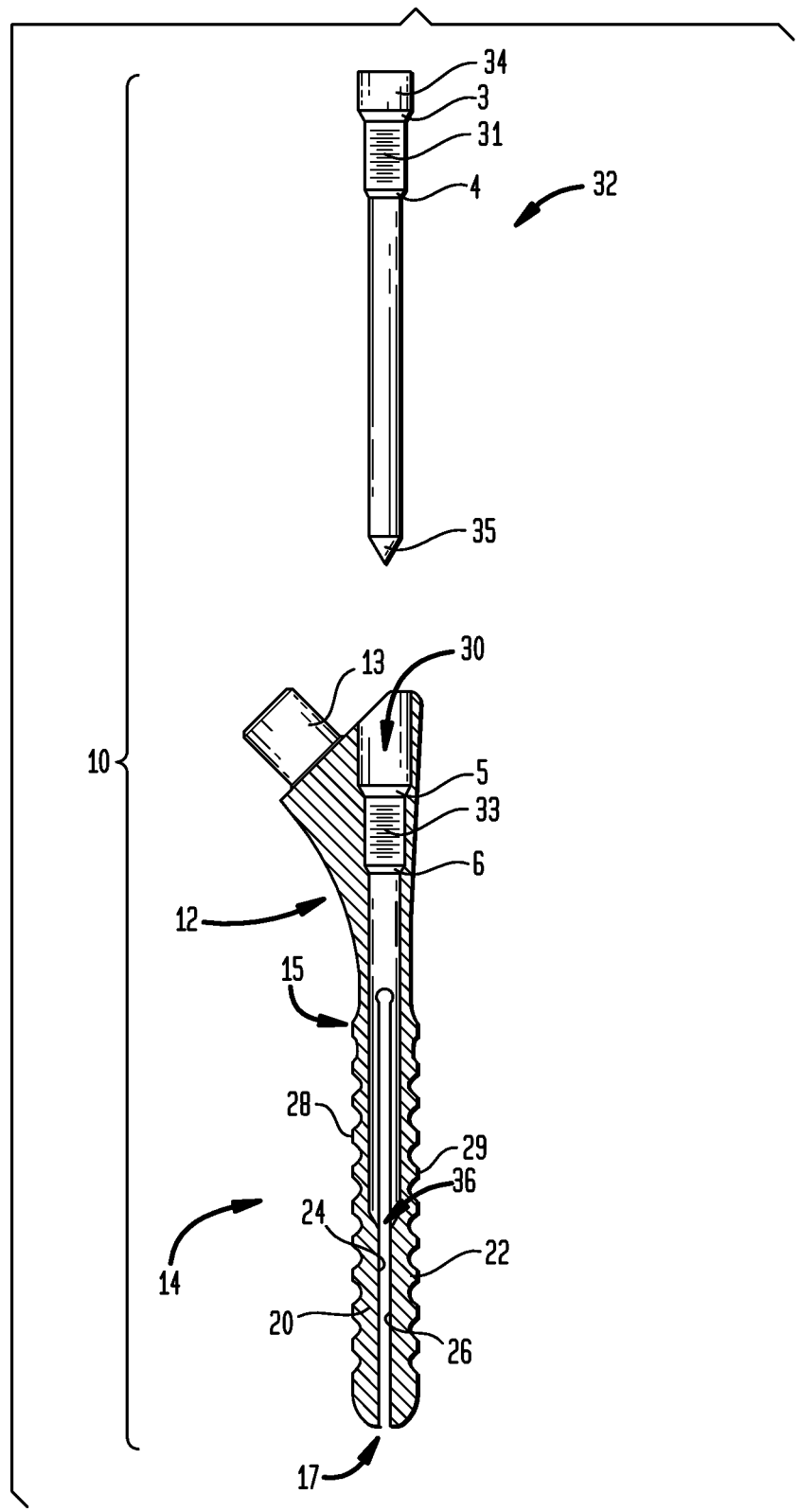
FIG. 8 is an exploded cross-section view of a trial according to an embodiment of the present invention.
Figure 9:
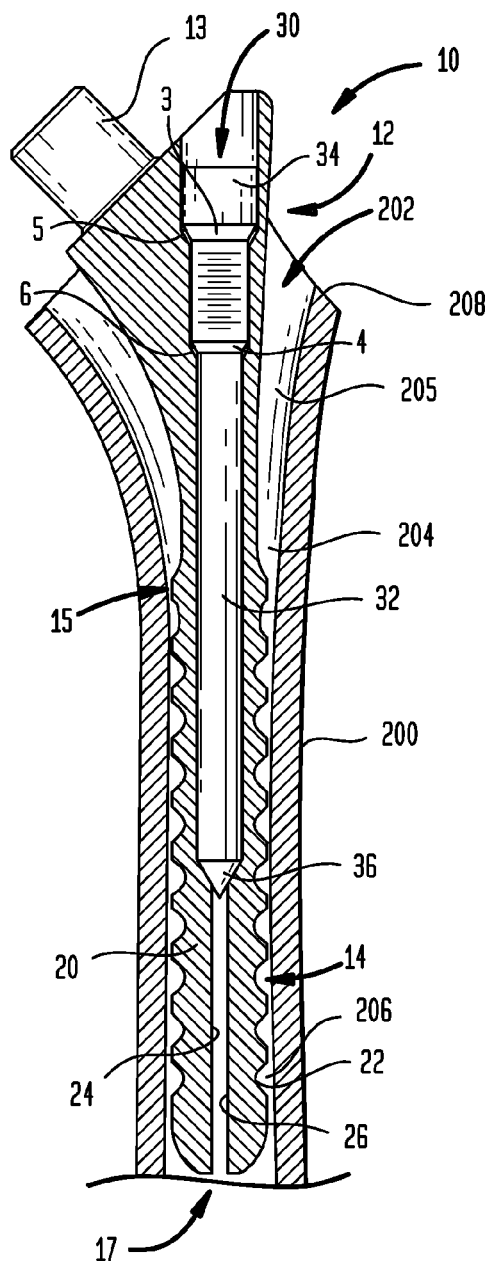
FIG. 9 is a cross-section view of a trial according to an embodiment of the present disclosure, wherein the trial is inserted in an opening formed in a proximal humerus.

As best shown in FIGS. 8 and 9, hole 30 includes a terminal end 36 which is located within distal portion 14, and is preferably located near the midpoint thereof. Terminal end 36 of hole 30 is preferably generally conical in shape so as to form a surface that is inclined from the interior surface of hole 30 to the first and second faces 24, 26 of first and second arms 20, 22. The distal end 35 of driver 32 is preferably in the shape of a wedge, and is preferably conical so as to match the shape of terminal end 36 of hole 30 and is able to rotate while maintaining contact therewith. Alternatively, distal end 35 can be rotatably affixed to the remainder of driver 32 and can fit within terminal end 36 of hole 30 so as to operatively engage terminal end 36 without rotating with respect thereto. Such an arrangement may serve to prevent wear of terminal end 36 which could be caused by rotating distal end 35 therein. The preferred conical shape driver end 35 and the complementary conical shape of terminal end 36 of hole 30 act together to effect movement of first arm 20 and second arm 22 with respect to each other. This is done, for example, by turning driver 32 with respect to hole 30 such that driver 32 moves distally within hole 30. The distal movement of driver 32 within hole 30 causes operative engagement of distal end 36 of driver 32 with terminal end of hole 30 such that first arm 20 and second arm 22 are forced outward with respect to each other, as shown in FIG. 10.

Figure 10:
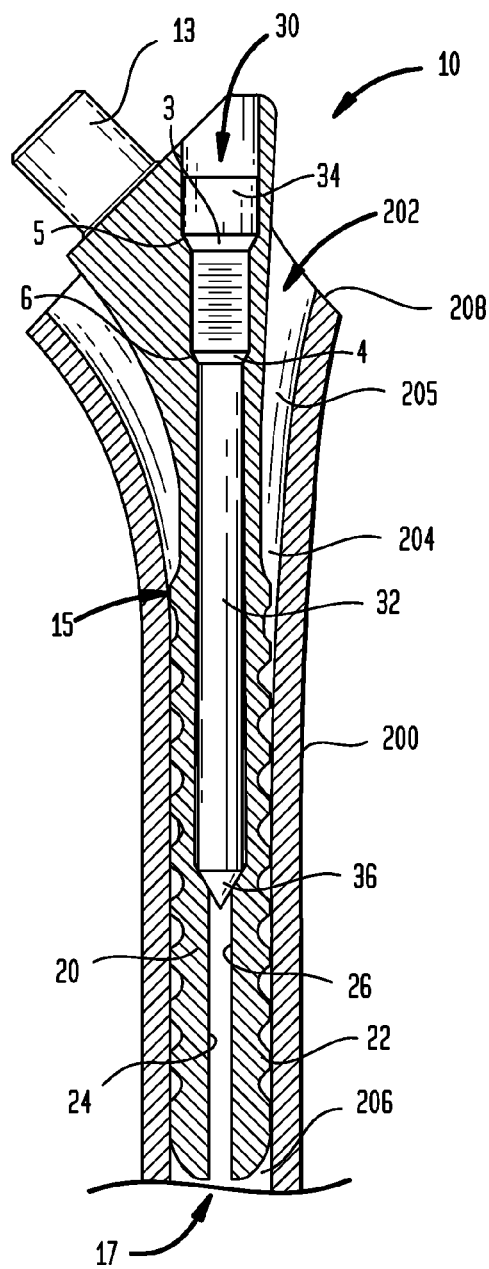
FIG. 10 is a cross-section view of a trial as shown in FIG. 9, wherein the distal portion of the trial is expanded to temporarily secure the trial within the opening formed in the proximal humerus.
Figure 11:
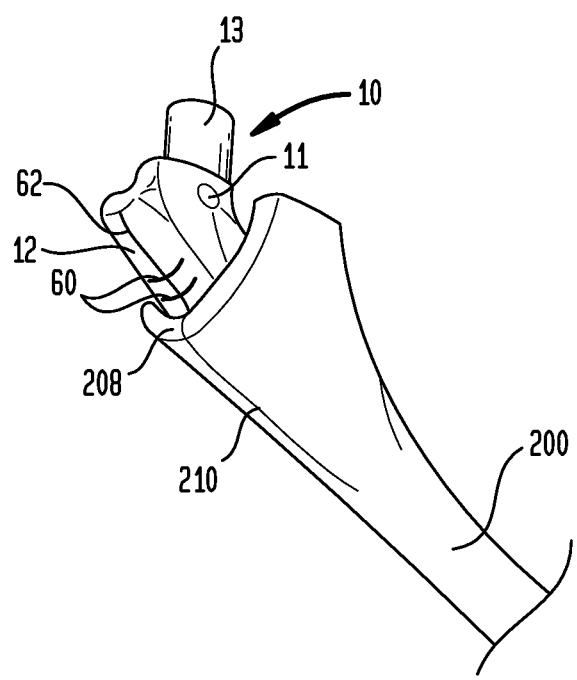
FIG. 11 is an isometric view of a trial according to an embodiment of the present invention in which the trial is inserted into an opening formed in a proximal humerus, the trial including indicia relating to the position thereof with respect to the proximal humerus.

As also shown in FIGS. 8-10, the portion of hole 30 that is formed in proximal portion 12 of trial 10 is shaped to conform to the corresponding shape of driver 32. In particular, hole 30 changes diameter at two chamfered portions 5, 6, one located above and one located below threaded portion 33. The chamfered portions 5, 6 of hole 30 correspond to chamfered portions 3, 4 of driver 32, as shown in FIGS. 9 and 10. In FIG. 9, trial 10 is illustrated with driver 32 not fully advanced within hole 30. In that position, the chamfered portions 3, 4 of driver 32 are spaced from the corresponding chamfered portions 5, 6 of hole 30, and the arms 20, 22 are not fully expanded against the interior surface 204 of opening 202 in humerus 200. In FIG. 10, driver 32 is advanced distally, causing the first and second arms 20, 22 to move into the second position, in which substantially all of distal portion 14 of trial 10 contacts the interior surface 204 of opening 202. In that position, the chamfered portions 3, 4 of driver 32 contact the chamfered portions 5, 6 of hole 30. Due to the change in diameter of hole 30 at chamfered portions 5, 6, driver 32 can not move distally any further within hole 30 when the chamfered portions 3, 4 of driver 32 contact the chamfered portions 5, 6 of hole 30. Thus, this contact limits the expansion of arms 20, 22 beyond the second position, as shown in FIG. 10.

The structure of outside surfaces 28, 29 of arms 20, 22 may include a series of intersecting groves 42, as shown in FIG. 2. This provides a texture to outside surfaces 28, 29 which creates friction between the inner surface of the prepared medullary canal and trial 10, when trial 10 is inserted therein. By including grooves 42 in both the proximal-distal direction and longitudinally, around the circumference of outside surfaces 28, 29, friction is created in two directions, which serves to secure trial 10 within the prepared medullary canal with respect to rotational and axial movement thereof when trial 10 is inserted into the prepared medullary canal and secured therein through expansion of distal end 14.

An alternative embodiment of trial 310 is shown in FIGS. 12-14 and includes a proximal portion 312 and a distal portion 314, the proximal portion having a post 313 extending therefrom along a longitudinal axis 316. Distal portion 314 extends distally from proximal portion 312 along a longitudinal axis 319 and includes a first arm 320, a second arm 321, and a third arm 322. Each arm 320, 321, and 322 includes a respective inwardly-directed face 324, 325, and 326. As shown in FIG. 14, a portion of each of faces 324, 325, and 326 is open to and spaced apart from at least a portion of each of the remaining faces. For example, a portion 324*a* of face 324 is open to a corresponding portion of face 325 and a portion 324*b* of face 324 is open to a corresponding portion of face 326. Further preferably, portion 324*a* of face 324 forms an angle of approximately 120 degrees with portion 324*b* of face 324. Further each arm 320, 321, and 322 includes a respective outside surface 327, 328, and 329.

Arms 320, 321, 322 are preferably shaped so as to be moveable from a first position to a second position by moving driver 332 within hole (not shown) in the distal direction. Preferably, distal portion 314 is shaped so that when arms 320, 321, 322 are in first position outside surfaces 327, 328, 329 arc have a tapered shape similar to that of arms 20 and 22 of trial 10, as discussed with respect to FIGS. 5-7. Further preferably, distal portion 314 is shaped that when arms 320, 321, 322 are in the second position, outside surfaces 327, 328, 329 form a substantially cylindrical shape.

Figure 15:
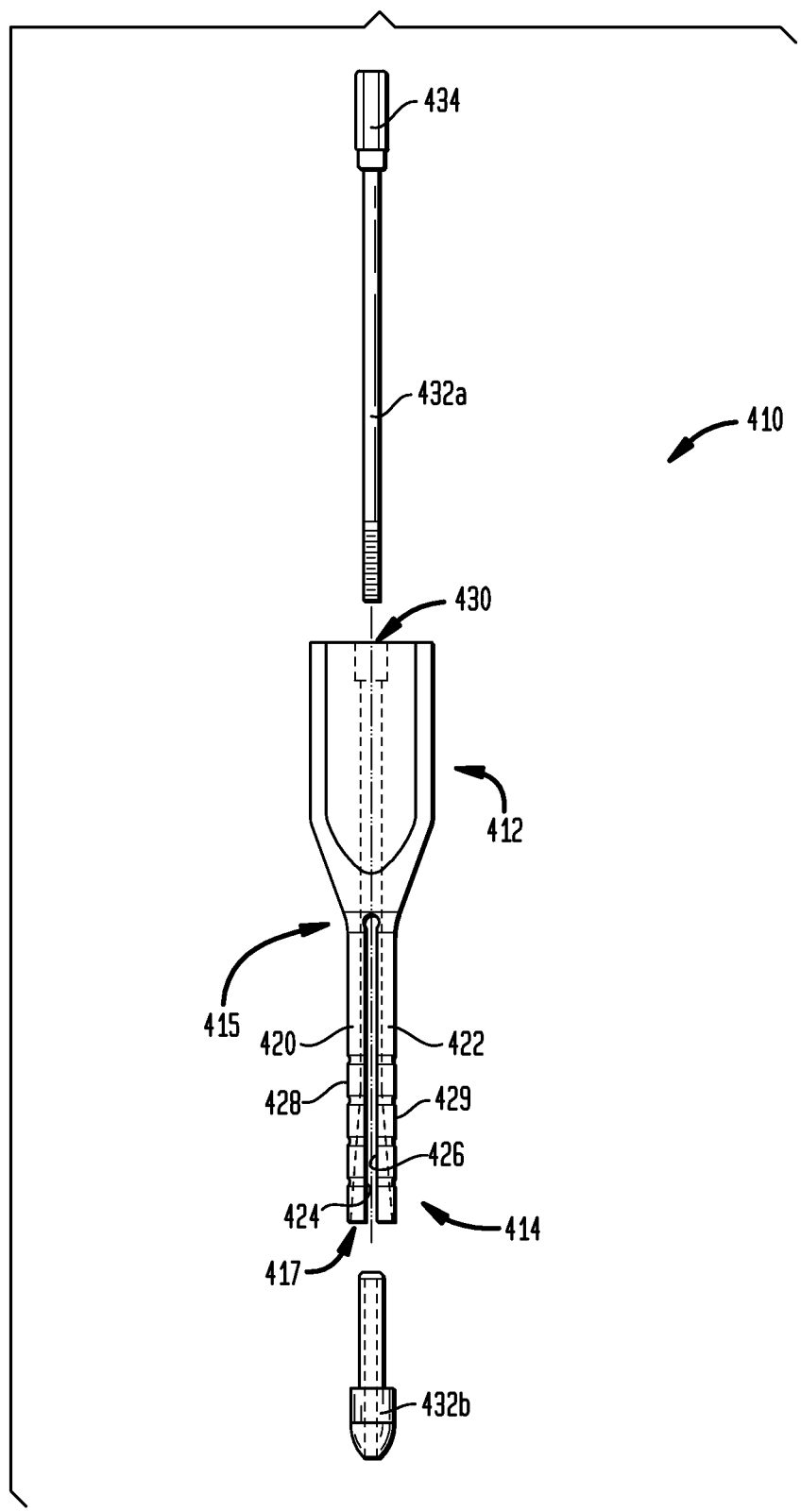
FIG. 15 is an exploded elevation view of a trial according to an embodiment of the present invention.

An additional alternative embodiment of trial 410 according to the present invention is shown in FIG. 15. Trial 410 includes a proximal portion 412 and a distal portion 414 projecting therefrom. Distal portion includes a first arm 420 and a second arm 422, each arm 420, 422 having a respective, inwardly-directed face 424, 426. Trial 410 also includes a driver mechanism comprised of a bolt 432*a* and a nut 432*b* that is assembled into cavity 430 that extends through proximal portion 412 and distal portion 414. Driver mechanism is operable to cause outward movement of arms 420, 422 with respect to each other from a first position to a second position by turning bolt 432*a* into nut 432*b* such that nut 432*b* is drawn into distal portion in a substantially proximal direction. The interior surface of cavity 430 is preferably inclined inwardly moving proximally from tip 417 of distal portion 414 so as to promote the movement of arms 420, 422 by proximal movement of nut 432*b*.

As discussed with respect to previous embodiments, outside surfaces 428, 429 are preferably tapered when arms 420, 422 are in the first position in a similar manner to that of arms 20, 22 as discussed with reference to FIGS. 5-7. Further, outside surfaces 428, 430 are preferably shaped that when arms 420, 422 are in the second position, outside surfaces 428, 429 form a substantially cylindrical shape.

A further embodiment of the present disclosure relates to a method for performing surgery using a trial 10 according to the embodiments discussed with reference to FIGS. 1-10. The method can be used, for example, during arthroplasty procedures involving a ball-and-socket type joint, preferably of a human patient, such as the hip or the shoulder. In the present example, the method is used during replacement of the humeral head with a prosthetic implant during shoulder arthroplasty. Generally, such a procedure involves gaining access to the shoulder joint through a retracted incision and removing the damaged humeral head. The proximal end of the humeral medullary canal is then shaped in order to accept an implant according to known methods which may include using a hand reamer to remove bone material until an appropriately-shaped opening 202 is formed in the proximal humerus 200 for receiving an implant. Typically, successive reamers of increasing size are used in order to form an opening of the desired size.

Once opening 202 is formed for receiving an implant, trialing is conducted to determine the proper size and location for the implant prior to implantation thereof. According to the present example, trialing includes inserting trial 10 according to the embodiments discussed with respect to FIGS. 1-10 (although any of the additional embodiments discussed herein could be used) into opening 202 in proximal humerus 200. Preferably, the particular trial 10 selected corresponds to the size of opening 202. Accordingly, a kit with a number of differently-sized trials 10 according to the embodiments discussed with respect to FIGS. 1-10 may be provided. Further, these differently-sized trials 10 may correspond to the increasingly-sized reamers, or other similarly acceptable devices, used to form opening 202 in proximal humerus 200. For example, the distal portion 14 of a trial 10 according to one embodiment can, for example, be of a size that substantially matches that of the largest of the successive reamers used to form opening 202 in proximal humerus 200 when first and second arms 20, 22 are in the second position.

Trial 10 for use in the method according to the present embodiment should be sized relative to opening 202 formed in proximal humerus 200 such that trial 10 can be slid into opening 202 and be temporarily secured into place by expanding distal portion 14 thereof, as discussed with respect to FIGS. 9 and 10. Preferably, at least a point on each of outside surfaces 28, 29 near tip 17 of distal portion 14 is spaced apart from the interior surface 204 of opening 202. Furthermore trial 10 is sized such that when first and second arms 20, 22 are in the first position, substantially all of each outside surface 28, 29 of arms 20, 22 located near proximal end 15 thereof is in contact with the proximal end 205 of interior surface 204 of opening 202. This sizing of trial 10 may help provide for accurate placement of trial 10 within humerus 200 prior to temporarily securing trial 10 therein. In an alternative arrangement, trial 10 may be sized such that substantially all of distal portion 14 is spaced apart from distal end 206 of interior surface 204 prior to expansion thereof.

Once trial 10 is inserted into humerus 200, it is visually inspected to determine if the correct size has been selected. This is done by comparing the size of the trial 10 to the size of opening 202. If the size of trial 10 selected is determined to be incorrect, another size is selected and inspected according to similar criteria. Once the correct size trial 10 has been selected, a trial head is assembled onto trial 10 by press-fitting the trial head (not shown) onto post 13. The particular trial head used can be selected by visual comparison to the resected humeral head. Trial 10 with the assembled head is then aligned within the joint so as to contact the articulating surface of the glenoid. In order to aid in rotational alignment of trial 10 within opening 202, proximal portion 12 may include a hole 11 formed transversely therethrough so as to extend from the anterior side to the posterior side thereof. Hole 11 is designed to be used in connection with a version rod 9 that is sized so as to slideably engage hole 11 and to extend away from trial 10 such that it can be used to impart a rotational force thereto. Preferably hole 13 includes a flat side 8 to mate with a flat side 7 formed on the version rod 9 so as to prevent rotation therebetween.

Distal portion 14 of trial 10 is then expanded to bring at least a point along distal portion near tip 17 into contact with interior surface 204 of opening 202. Preferably, distal portion 14 is tapered, as previously discussed with reference to FIGS. 8 and 9, such that expansion thereof causes substantially all of distal portion 14 to contact the interior surface 204 of opening 202. Such an arrangement at least somewhat evenly distributes the pressure formed by the expanded distal portion 14 of trial 10 on interior surface 204 of opening 202 formed in humerus 200. Uneven distribution of such pressure occurring, for example, near tip 17 of distal portion 14 can be problematic as it can cause damage to the humerus and can result in an insecure fit between distal portion 14 and opening 202, which can further lead to an unreliable assessment of the placement of trial 10. Preferably, expansion of distal portion 14 is effected by inserting a tool, preferably of the hex-wrench type, into head 34 of driver 32 and using the tool to turn driver 32 with respect to hole 30 so as to cause driver 32 to move distally within hole 30. As discussed with respect to FIGS. 9 and 10, trial 10 is preferably structured such that the distal movement of driver 32 within hole 30 causes first arm 20 and second arm 22 to move into the second position thereof.

Preferably, the desired expansion of distal portion 14 is achieved by rotating driver 32 through an angle of no more than 360o. More preferably, the desired expansion of distal portion 14 is achieved by rotating driver 32 through an angle of approximately 45o. The angle through which driver 32 must be rotated in order to secure trial 10 within opening 202 will vary with the shape of distal portion 14, particularly the distance by which outside surfaces 28, 29 are tapered, as well as the angle of the wedge formed on the end 35 of driver 32 and the matching angle of the inclined portion 36 of hole 32 and the pitch of the threaded sections 31, 33 of hole 30 and driver 32. The diameter of distal portion 14 of the selected trial 10 compared to the diameter of opening 202 may also affect the rotation of driver 32 necessary to achieve the desired expansion for distal portion 14.

Preferably, the taper formed in distal portion 14 should be such that expansion of less than 1 mm is necessary to secure trial 10 within opening 202. For example, when distal portion 14 of trial 10, as shown in FIGS. 1-9, is expanded such that outside surfaces 28, 29 of arms 20, 22 engage the interior surface 204 of opening 202, the distance between first face 24 and second face 26 increases by less than 1 mm at the points thereof nearest the tip 17 of distal portion 14. More preferably, the distance of expansion necessary for a point on distal portion 14 near tip 17 to engage interior surface 204 is about 0.5 mm.

Once trial 10, with a trial head assembled thereto, is secured in a position within opening 202, the position thereof is assessed for proper joint kinematics. This is conducted according to generally known methods and includes moving the arm of the patient so as to cause movement of the trial head with respect to the articulating surface of the glenoid (or a prosthetic articulating surface, if one is used to replace the articulating surface of the glenoid). If the position in which trial 10 is temporarily secured is determined to be unsatisfactory for providing proper joint kinematics, trial can be loosened from within the prepared humeral canal by withdrawing driver 32 within cavity 30. The position of trial 10 within opening 202 can then be adjusted, and trial 10 can be secured in that position by expansion of distal portion 14 as discussed above.

When a satisfactory position has been achieved for trial 10 within opening 202, the humerus 200 is moved so as to withdraw the trial head from the articulating surface of the glenoid. The position of trial 10 within opening 202 is then established. This is done using a series of height markings 60 and at least one version marking 62 (as shown in FIG. 1) included on proximal portion 12 of trial 10. Height 60 and version 62 markings correspond to similar markings that may be included on the implant that corresponds in size to trial 10. Height markings 60 are used to measure the height of trial 10 within, for example, the humerus 200 and are preferably used to measure the height of trial 10 with respect to the upper edge 208 of humerus 200, which is formed by the plane in which the proximal humerus has fractured. The corresponding markings on the implant are later used to position the implant at substantially the same height. Version marking 62 is then used to establish the rotational position of trial 10 within humerus 200. This may be done by extending the line of version marking 62 onto the humerus 200 forming line 210, which may be done, for example, using a laser. Line 210 is then used as a guide in making a matching line on the humerus by, for example, electrocautery. The corresponding version marking on the implant is then aligned with line 210 formed on humerus 200 to provide the proper rotational alignment of the implant. Additionally, proximal portion 12 of trial 10 can include features which correspond to similar features included on the corresponding implant, which may include, for example a plurality of circular features 64 corresponding to suture holes of an implant. These features 64 can be used to assure that the corresponding features of the implant are properly positioned when the implant is inserted into opening 202. For example, circular features 64 can be used to assess the location of suture holes of a corresponding implant while positioning trial 10 within opening 202 such that the suture holes included on the implant will be positioned so as to properly stretch muscles affixed thereto.

When the position of trial 10 within humerus 200 is established, distal portion 14 of trial 10 is loosened from within opening 202 by returning first and second arms 20, 22 to the first position thereof, preferably by inserting a tool into driver 32 and using the tool to cause proximal movement of driver 32 within hole 30. Trial 10 is then removed from the proximal humerus 200. An implant corresponding in size to the trial is then inserted into opening 202 formed in the proximal humerus 200. For example, an implant may correspond in size to a trial 10 used to assess joint kinematics and establish a position for the implant by having a stem that is similarly shaped with respect to distal portion 14 of trial 10 but is smaller in cylindrical diameter. The smaller diameter of the stem of the implant in this example compensates for the cement mantle interposed between the stem of the implant and the interior surface 204 of opening 202. Preferably, the stem of the implant is about 2 mm smaller in diameter than distal portion 14 of the corresponding trial 10. The implant is then aligned, as discussed above, and is secured in place using a bone cement composition. The procedure is then completed by reattaching the bone fragments and any muscles or tendons which were detached during the operation and closing the wound site.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for performing a surgical procedure, comprising:
   introducing a trial at least partially into a prepared bone canal within a bone, the trial having an expandable bone engaging surface and a feature which is operable to cause expansion of the bone engaging surface;
   manipulating the trial into a first position within the prepared bone canal;
   temporarily securing the trial within the prepared bone canal by operating the feature of the trial so as to cause the bone engaging surface to expand and engage an interior surface of the prepared bone canal;
   removing the trial from the prepared bone canal during the surgical procedure;
   introducing a stem of an implant having a fixed outer diameter at least partially into the prepared bone canal during the surgical procedure; and
   affixing the implant within the prepared bone canal using cement during the surgical procedure such that a cement mantle is interposed between the stem and the bone.

2. The method of claim 1, wherein the prepared bone canal is proximate a joint between the bone and a second bone.

3. The method of claim 2, further comprising:
   assembling a head onto a post projecting from a proximal portion of the trial, the head having a first articulating surface;
   positioning the head so as to engage a second articulating surface associated with the joint; and
   testing the joint to determine if a proper position for the trial has been achieved.

4. The method of claim 1, further comprising reversing the expansion of the bone engaging surface.

5. The method of claim 4, wherein the feature of the trial is operable to reverse the expansion of the bone engaging surface.

6. The method of claim 4, further comprising:
   manipulating the trial into a second position within the prepared bone canal after the step of reversing the expansion of the bone engaging surface; and, subsequently,
   temporarily securing the trial within the prepared bone canal by operating the feature of the trial so as to cause the bone engaging surface to re-engage the interior surface of the prepared bone canal.

7. The method of claim 1, further comprising operating the feature of the trial to reverse the expansion of the bone engaging surface before the step of removing the trial from the prepared bone canal.

8. The method of claim 1, wherein the trial includes a visual indicia relating to the position of the trial within the prepared bone canal, and wherein the method further comprises using the visual indicia to establish a location of the trial relative to the bone.

9. The method of claim 8, wherein the implant includes an indicia that corresponds to the visual indicia of the trial.

10. The method of claim 8, further comprising manipulating the implant into a position that corresponds to the first position of the trial using the indicia of the implant.

11. The method of claim 10, wherein the visual indicia of the trial includes a plurality of markings on the proximal portion thereof, the markings relating to a position of the trial with respect to the prepared bone canal in a proximal-distal direction.

12. The method of claim 10, wherein the visual indicia of the trial includes a marking on the proximal portion thereof, the marking relating to a rotational position of the trial with respect to the prepared bone canal.

13. The method of claim 1, wherein the trial includes a proximal portion having a hole extending transversely therethrough, the hole being adapted to receive a rod, and wherein the step of manipulating the trial into a first position within the prepared bone canal includes applying a force to the rod so as to rotate the trial within the prepared bone canal.

14. The method of claim 1, wherein the trial includes a proximal portion and a distal portion, the distal portion of the trial including a first arm and a second arm, the first and second arms extending distally away from the proximal portion of the trial, wherein the expandable bone engaging surface is formed on the first and second arms, and wherein the step of temporarily securing the trial within the prepared bone canal includes causing a portion of the first arm and a portion of the second arm to move outwardly away from one another such that the bone engaging surface forms a substantially cylindrical shape.

15. The method of claim 14, wherein the trial includes a cavity extending through the proximal portion and into the distal portion and a driver adapted for sliding engagement with the cavity, and wherein the step of temporarily securing the trial within the prepared bone canal includes moving the driver distally within the cavity.

16. The method of claim 15, wherein the driver includes a threaded portion near a proximal end thereof, wherein the proximal portion of the trial includes a threaded portion therein adapted to engage the threaded portion of the driver, and wherein the step of moving the driver distally within the cavity includes rotating the driver with respect to the cavity.

17. The method of claim 14, wherein the implant has a stem having a first cylindrical diameter and the distal portion of the trial has a second cylindrical diameter, the first cylindrical diameter being smaller than the second cylindrical diameter.

18. The method of claim 14, wherein, prior to the step of temporarily securing the trial within the prepared bone canal, the bone engaging surface is tapered along a proximal-distal plane therethrough such that a tip portion of the bone engaging surface is spaced apart from the interior surface of the prepared bone canal and at least a portion of an upper portion of the bone engaging surface contacts the interior surface of the prepared bone canal, and wherein the step of temporarily securing the trial within the prepared bone canal includes causing a portion of the first arm and a portion of the second arm to move outwardly away from one another such that at least a portion of the tip portion of the bone engaging surface contacts the interior surface of the prepared bone canal.

19. The method of claim 1, wherein the bone engaging surface is on a distal portion of the trial extending along a longitudinal axis, and wherein a cross-section of the distal portion perpendicular to the longitudinal axis substantially defines a circle when the bone engaging surface is in an expanded position, the cross-section being non-circular when the bone engaging surface is in an unexpanded position.

20. A method for performing a surgical procedure, comprising:
   introducing a trial at least partially into a prepared bone canal within a bone, the trial having an expandable bone engaging surface and a feature which is operable to cause expansion of the bone engaging surface;

manipulating the trial into a first position within the prepared bone canal;

temporarily securing the trial within the prepared bone canal by operating the feature of the trial so as to cause the bone engaging surface to expand and engage an interior surface of the prepared bone canal;

removing the trial from the prepared bone canal during the surgical procedure; and affixing a nonexpendable stem of an implant within the prepared bone canal during the surgical procedure.

21. A method for performing a surgical procedure, comprising:

introducing a trial at least partially into a prepared bone canal within a bone, the trial having an expandable trial stem and a feature which is operable to cause expansion of the trial stem into an expanded configuration, the trial stem having a first diameter in the expanded configuration;

manipulating the trial into a first position within the prepared bone canal;

temporarily securing the trial within the prepared bone canal by operating the feature of the trial so as to cause the trial stem to expand into the expanded configuration and engage an interior surface of the prepared bone canal;

removing the trial from the prepared bone canal during the surgical procedure; and affixing a stem of an implant having a second diameter to the bone within the prepared bone canal during the surgical procedure, the second diameter being smaller than the first diameter so as to leave a gap between the interior surface of the bone canal and implant stem.

* * * * *